(12) United States Patent
Ribbing et al.

(10) Patent No.: US 10,360,344 B2
(45) Date of Patent: Jul. 23, 2019

(54) DIAGNOSTIC TECHNIQUES FOR CONTINUOUS STORAGE AND JOINT ANALYSIS OF BOTH IMAGE AND NON-IMAGE MEDICAL DATA

(75) Inventors: Carolina Ribbing, Aachen (DE); Martin Weibrecht, Aachen (DE); Peter K. Bachmann, Wuerselen (DE)

(73) Assignee: Koninklijke Philips N.V., Eindhoven (NL)

( * ) Notice: Subject to any disclaimer, the term of this patent is extended or adjusted under 35 U.S.C. 154(b) by 1140 days.

(21) Appl. No.: 13/513,428

(22) PCT Filed: Nov. 17, 2010

(86) PCT No.: PCT/IB2010/055237
§ 371 (c)(1),
(2), (4) Date: Jun. 1, 2012

(87) PCT Pub. No.: WO2011/070461
PCT Pub. Date: Jun. 16, 2011

(65) Prior Publication Data
US 2012/0290324 A1   Nov. 15, 2012

Related U.S. Application Data (60) Provisional application No. 61/285,202, filed on Dec. 10, 2009.

(51) Int. Cl.
*G06Q 50/00* (2012.01)
*G06F 19/00* (2018.01)
*G16H 50/20* (2018.01)

(52) U.S. Cl.
CPC ........... *G06F 19/321* (2013.01); *G16H 50/20* (2018.01)

(58) Field of Classification Search
CPC ........ G06Q 50/22; G06Q 50/24; G06Q 40/08; G06Q 10/10; G06F 19/322; G06F 17/30;
(Continued)

(56) References Cited

U.S. PATENT DOCUMENTS

| 5,878,746 A | 3/1999 | Lemelson et al. |
| 7,640,051 B2 | 12/2009 | Krishnan et al. |

(Continued)

FOREIGN PATENT DOCUMENTS

| JP | H0314027 A | 1/1991 |
| JP | 3223967 | 10/1991 |

(Continued)

OTHER PUBLICATIONS

Sboner A. et al. (2003) "A multiple classifier system for early melanoma diagnosis", Artificial Intelligence in Medicine, vol. 27, No. 1, pp. 29-44, (XP55005913).*

(Continued)

*Primary Examiner* — Tran N Nguyen (57) ABSTRACT

An apparatus comprises: a database (30) storing medical data including image medical data and non-image medical data for a plurality of patients; a digital processor (40) configured to (i) generate a features vector (56) comprising features indicative of a patient derived from patient medical data stored in the database including both patient image medical data and patient non-image medical data and (ii) perform multivariate analysis (64) on a features vector generated for a patient of interest to determine a proposed diagnosis for the patient of interest; and a user interface (42) configured to output a human perceptible representation of the proposed diagnosis for the patient of interest.

17 Claims, 3 Drawing Sheets

(58) Field of Classification Search
CPC ........ G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00

See application file for complete search history.

(56) References Cited

U.S. PATENT DOCUMENTS

| | | | |
|---|---|---|---|
| 7,912,528 | B2 | 3/2011 | Krishnan et al. |
| 2005/0020903 | A1 | 1/2005 | Krishnan et al. |
| 2005/0049497 | A1* | 3/2005 | Krishnan ............... G06F 19/321 600/437 |
| 2009/0006132 | A1 | 1/2009 | Avinash et al. |
| 2012/0290324 | A1 | 11/2012 | Ribbing et al. |

FOREIGN PATENT DOCUMENTS

| | | |
|---|---|---|
| JP | 9257790 A | 10/1997 |
| JP | 20120542641 A | 10/1997 |
| JP | 2005309616 A | 11/2005 |
| WO | 2005001740 A2 | 1/2005 |

OTHER PUBLICATIONS

Marzi et al, "Relationships Between Rectal Wall Dose-Volume Constraints and Radiobiologic Indices of Toxicity for Patients With Prostate Cancer", Int. J. Radiation Oncology Biol. Physl, vol. 68, No. 1, 2007, pp. 41-49.

Pinkawa et al, "Prostate Position Variability and Dose-Volume Histograms in Radiotherapy for Prostate Cancer With Full and Empty Bladder", Int. J. Radiation Oncology Biol. Physl, vol. 64, No. 3, 2006, pp. 856-861.

Vavassori et al, "Predictors for Rectal and Intestinal Acute Toxicities During Prostate Cancer High-Dose 3D-CRT: Results of a Prospective Multicenter Study", Int. J. Radiation Oncology Biol. Physl, vol. 67, No. 5, 2007 pp. 1401-1410.

Pinkawa et al, "Low-Grade Toxicity After Conformal Radiation Therapy for Prostate Cancer-Impact of Bladder Volume", Int. J. Radiation Oncology Biol. Physl, vol. 64, No. 3, 2006, pp. 835-841.

Sohn et al, "Incidence of Late Rectal Bleeding in High-Dose Conformal Radiotherapy of Prostate Cancer Using Equivalent Uniform Dose-Based and Dose-Volume-Based Normal Tissue Complication Probability Models", Int. J. Radiation Oncology Biol. Physl, vol. 67, No. 4, 2007, pp. 1066-1073.

Calhoun et al, "Identification of Multimodal MRI and EEG Biomarkers Using Joint-ICA and Divergence Criteria", IEEE, 2007, pp. 151-156.

Munbodh et al, "Dosimetric and Anatomic Indicators of Late Rectal Toxicity After High-Dose Intensity Modulated Radiation Therapy for Prostate Cancer", Med. Phys, vol. 35, No. 5, May 2008, pp. 2137-2150.

Menard et al, "Discovering Clinical Biomarkers of Ionizing Radiation Exposure With Serum Proteomic Analysis", Cancer Research, vol. 66, No. 3, 2006, pp. 1844-1850.

Jiazheng et al, "Characterization of Mammographic Masses Based on Level Set Segmentation With New Image Features and Patient Information", Medical Physics, vol. 35, No. 1, 2008, pp. 280-290.

Sboner et al, "A Multiple Classifier System for Early Melanoma Diagnosis", Artificial Intelligence in Medicine, vol. 27, No. 1, 2003, pp. 29-44.

* cited by examiner

DIAGNOSTIC TECHNIQUES FOR CONTINUOUS STORAGE AND JOINT ANALYSIS OF BOTH IMAGE AND NON-IMAGE MEDICAL DATA

The following relates to the medical arts, medical diagnostic arts, oncology arts, and related arts.

In the treatment of medical conditions such as cancers, cardiac disease, or so forth, a number of different imaging and nonimaging diagnostics are typically marshaled to provide complementary patient information for making complex and difficult medical decisions. As an illustrative example, prostate cancer treatment is complex and involves a delicate balance between optimization of clinical benefits, life expectancy and minimization of treatment-related side-effects. In some patients, radiation therapy treatment is indicated. Radiation treatment of prostate cancer is given in several fractions, typically daily over a period of several weeks, such as a total dose of 76 Gy in 38 fractions over a period of 8 weeks. Radiotherapeutic treatment options include external beam therapy (ERT), that is, conformal radiation therapy where the radiation is delivered to the diseased area while attempting to spare surrounding tissue. Conformal radiation therapies include 3D conformal radiation therapy and intensity modulated radiation therapy (IMRT). The maximum radiation dose that can be given is limited by the tolerance of normal tissues within the radiation field. The radiation response varies considerably between individuals and the tolerance of the most sensitive subjects limits the dose that can be given to the population as a whole which may limit the chance of tumour cure. Ionizing radiation induces orchestrated response cascades at cellular as well as tissue level. The responses involve differential regulation of several cytokine cascades, which together impact the resulting normal tissue damage. Radiation-induced damage of normal tissue involves many different cell types and the long-term tissue composition is likely to change as a result of radiation. For example, the number of inflammatory cells and the amount of fibrotic tissue increase after irradiation.

Before radiation treatment of prostate cancer starts, the patient is normally imaged using various techniques. Needle biopsies may be taken under transrectal ultrasound. (TRUS) guidance. However, the TRUS image resolution is not high enough for detection of early-stage prostate cancer. For staging of more advanced prostate cancer, anatomical imaging modalities like x-ray computed tomography (CT) and magnetic resonance (MR) imaging can be used, for example to detect extracapsular tumour extensions, seminal vesicle involvement, and abnormal sizes of lymph nodes. Functional imaging modalities can also be employed, e.g. positron-emission tomography (PET) using cholin tracers, single-photon emission computed tomography (SPECT), and special MR schemes (MR spectrometry, Combidex® for lymph-node staging). For planning and simulation of the radiotherapy, a planning CT scan is recorded, tumor and sensitive organs are outlined on axial slices, and the geometrical centre of the tumor volume is calculated. Local control of a prostate tumour increases with the administered radiation dose. However, by increasing the radiation dose, the risk of complications caused by injury to bladder, urethra, and rectum also increases. The incidence of complications is also associated with the size of the irradiated volume. There are several predictors of such complications, so-called radiation toxicity or radiotherapy side-effects. For example, the mean rectal dose correlates with acute rectal and intestinal toxicity in 3D conformal radiotherapy of prostate cancer, whereas hormonal therapy and the use of anticoagulants are considered protective. More precisely, a larger mean rectal dose is associated with a larger bleeding risk, larger irradiated volumes are associated with stool frequency, tenesmus, incontinence, and bleeding. Hormonal therapy is protective against frequency and tenesmus, hemorrhoids are associated with a larger risk of tenesmus and bleeding, and diabetes associates with diarrhea. The dose to the rectal intestinal wall can be analyzed in more detail using dose-volume histograms (DVH) from 3D radiotherapy treatment planning systems. In this way, the volume of rectal wall receiving the highest dose (e.g. the wall volume receiving >70 Gy), the irradiated rectum area, target and rectum size may in some cases be more predictive of late rectal toxicity than the mean rectal dose. Target volume and height, rectum surface area and average cross-sectional area have also been shown to correlate with radiotoxicity. The bladder volume and the percentage of the bladder volume which receives 1019% of the prescribed dose is correlated with urinary function and patient questionnaire bother scores. Furthermore, a full bladder improves the position consistency of the prostate and lowers the bladder and bowel doses.

The forgoing prostate cancer example is merely an illustration of the kids of complex interrelationships between various imaging and nonimaging medical data that can be synergistically exploited to identify and clarify treatment options. Monitoring of radiation treatment of prostate cancer can usefully combine information provided by imaging methods with information from nonimaging methods such as molecular information provided by in vitro diagnostics (IVD), and/or mass spectrometric protein patterns from mass spectrometry which can be used for early diagnostics of a wide variety of disease states as well as for other purposes such as detection of radiation exposure from patient serum.

The foregoing prostate cancer example is merely one example of interrelated imaging and non-imaging diagnostics. As another example, consider high-risk plaque in arteries, which is a major source of diseases such as stroke and acute myocardial infarction. These diseases often occur without prior symptoms, because the source is the rupture of a plaque that has not been haemodynamically relevant. Therefore, significant effort is put into clinical research to characterize the vulnerability of plaque by diagnostics such as molecular markers and imaging. Several risk factors are known: lifestyle (smoking or other high-risk behavior), cholesterol levels and further molecular markers. Additionally, plaque characteristics derived from image data, in particular structural elements (e.g. intima medial thickness) and metabolic parameters (e.g. FDG uptake), are evaluated. A combination of such imaging and non-imaging diagnostics is useful—however, no singular diagnostic modality is sufficient to assess the risk of plaque rupture.

More generally, the sensitivity and specificity of an individual diagnostic test or a single diagnostic parameter is limited. When clinicians evaluate diagnostic images or non-imaging diagnostic patient data such as biomarker parameters individually, certain disease conditions, such as the onset of side effects, may not be promptly detected or may not be detected at all. Conversely, an individual test may show positive for a disease condition that is not actually present.

In sum, it is known that combining various kinds of image and non-image medical data can be more probative than analyzing a single diagnostic test. This is why a patient typically undergoes multiple different kinds of tests during the diagnostic phase and to assess progress of the treatment phase. Diagnostic approaches combine imaging studies and other diagnostic tests such as IVD tests, histopathological data, and so forth.

However, existing approaches do not promote synergistic analysis of image and non-image medical data. Such synergistic analysis may be of high dimensionality and entails identifying relevant parameters and determining subvolumes in the resulting parameter space that optimally discriminate disease conditions. Problematically, imaging and nonimaging data are acquired and collected at various point in time, in different departments, or even at different medical facilities. The acquisition and, in some cases, analysis of site disparate data at different departments, different laboratories, or even different medical facilities ensures that the analysis docs not benefit from other complementary medical data. Moreover, data acquisition is scheduled based on the availability of the various image and nonimage medical laboratories and facilities, so that data acquisition order varies wildly from patient to patient. As a result, a complete set of medical data from complementary image or nonimage diagnostic modalities may be unavailable at the time of analysis. In some cases, this can result in medical analyses or diagnoses being made without crucial pieces of data.

The following provides new and improved apparatuses and methods which overcome the above-referenced problems and others.

In accordance with one disclosed aspect, an apparatus comprises: a database storing medical data including image medical data medical data for a plurality of patients; a digital processor configured to generate a features vector comprising features indicative of a patient derived from patient medical data stored in the database.

In accordance with another disclosed aspect, a diagnostic method comprises: maintaining a database storing medical data including image medical data and non-image medical data for a plurality of patients; generating features vectors corresponding to patients of the database, a features vector corresponding to a patient comprising features indicative of the corresponding patient derived from medical data for the corresponding patient stored in the database including both image medical data and non-image medical data; wherein at least the generating operation is performed by a digital processor.

In accordance with another disclosed aspect, a digital processor is configured to perform a diagnostic method as set forth in the immediately preceding paragraph. In accordance with another disclosed aspect, a storage medium stores instructions executable on a digital processor to perform a diagnostic method as set forth in the immediately preceding paragraph.

One advantage resides in facilitating joint data analysis in order to obtain information from synergistic combinations of image and non-image medical data.

Another advantage resides in ensuring that relevant data are available when generating a medical diagnosis.

Further advantages will be apparent to those of ordinary skill in the art upon reading and understanding the following detailed description.

Figure 1:
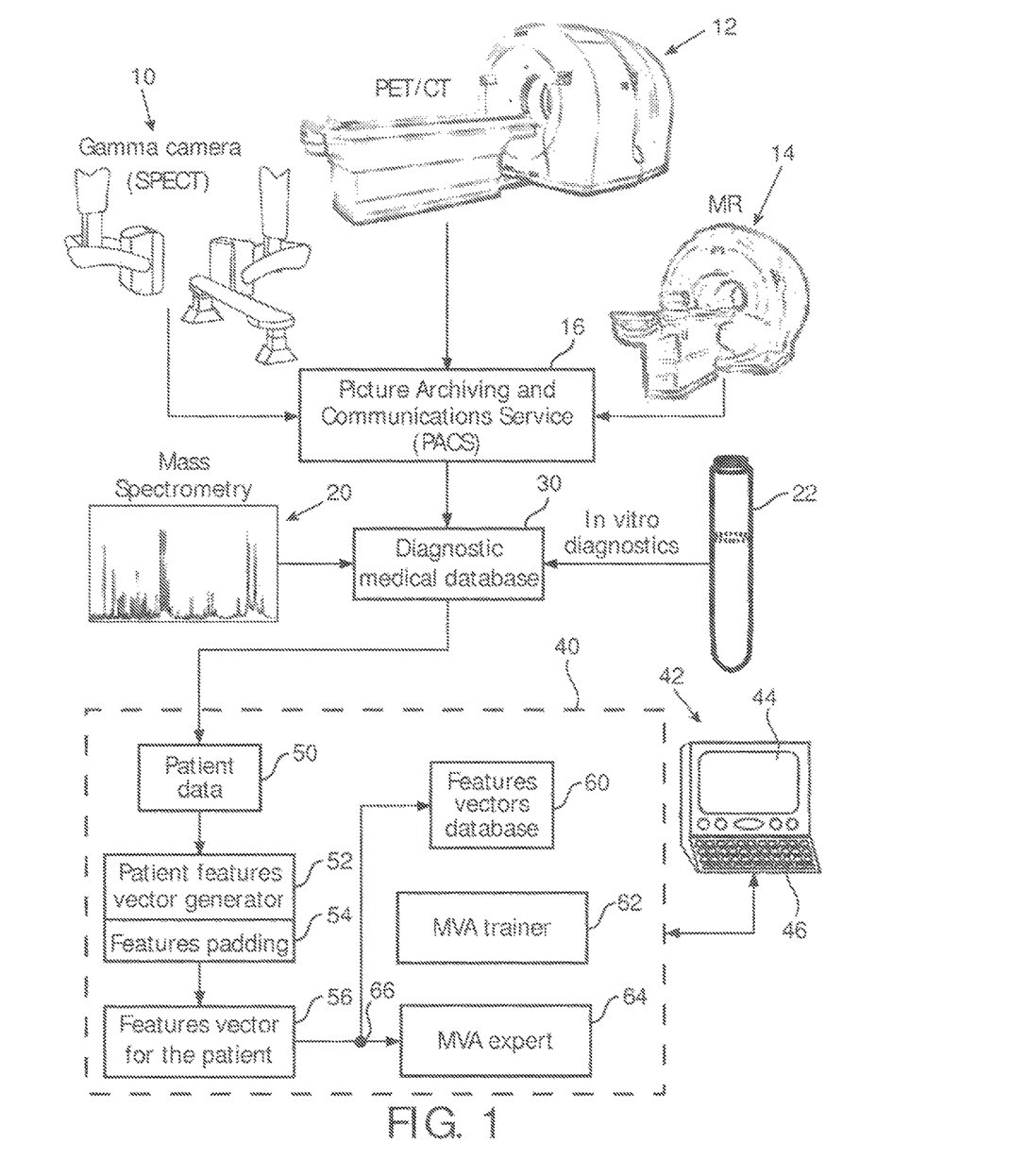
FIG. 1 diagrammatically illustrates a medical diagnostic apparatus including various medical diagnostic modalities and apparatus for synergistically analyzing image and non-image data acquired by these various medical diagnostic modalities.

With reference to FIG. 1, a plurality of representative medical diagnostic apparatuses, laboratories, or other facilities are shown as illustrative examples. FIG. 1 includes: a gamma camera 10 which in the illustrated embodiment is a Skylight™ gamma camera (available from Koninklijke Philips Electronics N.V., Eindhoven, The Netherlands); a hybrid PET/CT imaging system 12 which in the illustrated embodiment is a GEMINI™ PET/CT imaging system (available from Koninklijke Philips Electronics N.V., Eindhoven, The Netherlands); and a magnetic resonance (MR) imaging system 14 which in the illustrated embodiment is an Achieva™ MR system (available from Koninklijke Philips Electronics N.V., Eindhoven, The Netherlands). The gamma camera 10 is configured to acquire single photon emission computed tomography (SPECT) images. The hybrid PET/CT imaging system 12 is configured to acquire PET images and CT images. The MR system 14 is configured to acquire MR images. The imaging systems 10, 12, 14 are illustrative examples, and in general the diagnostic techniques disclosed here can be practiced using various types of imaging systems, such as various SPECT imaging systems, various PET imaging systems, various CT imaging systems, various MR imaging systems, various ultrasound imaging systems, various fluoroscopy imaging systems, various optical imaging systems, and so forth, as well as various hybrids of such imaging systems.

In the illustrated embodiment, an optical picture archiving and communication system (PACS) 16 provides a central database for archiving image medical data acquired by various imaging modalities and for accessing the archived image medical data. As used herein, the term "image medical data" encompasses acquired images (including CINE sequences), source data such as list-mode image data acquired by PET or CT images or k-space samples acquired by an MR imager, associated data such as electrocardiographic (ECG) data acquired to provide cardiac gating of the images, and medical image data derived from images as part of an imaging session, such as dimensions of organs, dose-volume histograms (DVHs), image-derived functional parameters such as cardiac stroke volume or standardized uptake value (SUV), or so forth. Medical image data derived from images may be generated at the imaging facility and stored in the PACS 16, or may be generated later based on images stored in the PACS 16.

With continuing reference to FIG. 1, a plurality of non-image medical diagnostic apparatuses, laboratories, or other facilities are also represented, namely: a mass spectrometer 20 configured to acquire proteomic data or other mass spectrometric data or data derived from mass spectra; and an in vitro diagnostic facility 22 configured to acquire in vitro diagnostic (IVD) data such as proteomic or genomic molecular information from drawn blood or other (fluid) samples, and including histological data and so forth. The non-image medical facilities 20, 22 are illustrative examples, and in general the diagnostic techniques disclosed here can be practiced using various types of non-image diagnostic facilities, such as various mass spectrometry apparatus or facilities, various IVD apparatuses or facilities, various histopathology diagnosis apparatuses or facilities, and so forth, as well as various hybrids of such apparatuses or facilities. Other sources of non-image medical data include patient questionnaires, patient medication data, recorded physiological parameters such as heart rate, blood pressure, and so forth.

A database 30 is configured to store medical data for a plurality of patients. The stored medical data includes both image medical data acquired by the medical imagers 10, 12, 14 (or by different, additional, or other medical imagers) and non-image medical data acquired by the non-image diagnostic apparatuses or facilities 20, 22 (or by different, additional, or other non-image diagnostic apparatuses or facilities). Stored data are suitably tagged with metadata identifying data type, data source, acquisition date, laboratory identification, and other relevant information. Medical data are stored in the database 30 as the data are acquired, and accordingly at any given point in time the stored medical data pertaining to a particular patient may be "incomplete" in the sense that certain tests ordered by medical personnel may not yet have been performed, or certain tests may not yet have been ordered. Moreover, it is to be appreciated that storage of data in the database 30 is to fee broadly construed as encompassing storage of pointers or other links to data that may physically reside elsewhere. For example, a medical image may be physically stored in the PACS 16 and a pointer or link to the medical image stored in the database 30, in which case the medical image is considered herein to be "stored" in the database 30.

A digital processor 40 is configured to perform analysis of the medical data and non-image medical data stored in the database 30 in order to generate a proposed diagnosis for a patient of interest. As used herein, the term "digital processor" is to be broadly construed as encompassing microprocessors, microcontrollers, and the like as well as digital devices embodying such a microprocessor or microcontroller, such as a computer, network server, Internet-based server, or so forth. The digital processor 40 may optionally also control storage of medical data in the database 30, or, alternatively, a different digital processor (not shown) may control storage of medical data in the database 30. The proposed diagnosis may, for example, include one or more of the following diagnoses: (1) a medical condition; (2) a stage of a medical condition; (3) a treatment side effect; (4) a treatment response; or so forth. Moreover, the proposed diagnosis optionally includes (one or more diagnoses together with) corresponding probabilities indicative of likelihood of each of the one or more diagnoses.

A user interface 42 enables a user to interact with the digital processor 40 to request a diagnosis for a patient of interest, and enables the user to view the proposed diagnosis or other information from the database 30. Toward this end, the illustrated user interlace includes at least one display 44 and at least one user input device 46 such as an illustrated keyboard, or a mouse or other pointing device, or a touch screen, or so forth. The user interface 42 also typically includes a digital processor for controlling operation of the user interface 42—this digital processor may be the same digital processor 40 that is configured to perform analysis of the medical data and non-image medical data stored in the database 30 in order to generate a proposed diagnosis for a patient of interest, or may be a different digital processor (not shown).

The database 30 continuously performs joint data collection of image medical data and non-image medical data for a plurality of patients (such as for all patients treated at a hospital or other medical facility, or all patients treated by a network of hospitals, or so forth). The continuous collection of medical data in the database 30 makes available a large, and ever-increasing data set that can be used in a learning mode to construct a multivariate analysis (MVA) which can be applied to a patient of interest in order to generate the proposed diagnosis. In MVA, a multi-dimensional space defined by medical diagnostic test results and parameters derived from various diagnostic procedures is analyzed to identify relevant discriminating parameters and respective multidimensional subvolumes, which describe specific disease conditions. The term multivariate analysis (MVA) as used herein is intended to encompass any multiple-parameter or multiple-variable analysis, for example including that not limited to) polynomial models, various statistical analyses, Monte Carlo simulations, or so forth.

Toward this end, medical data for the patients are stored in the database 30 together with metadata providing relevant reference values, calibration and normalization values, error estimates, dates of sample collection and analysis, and so forth. The MVA operates on features that are extracted from the medical data. Relevant features may be provided by medical images, such as distances between organs within a region of interest (e.g., the distance between rectum, bladder or prostate), or organ-specific dimensions such as intestinal wall thickness, prostate diameter, prostate volume, or so forth. Relevant features may also be provided by non-image medical data such as mass specter or IVD test results. The multiplicity of features may be outputted in human perceptible format (for example, displayed on the display 44 of she user interface 42), or may be jointly analyzed via MVA by the digital processor 40 to arrive at an individual side-effect, health risk, treatment recommendation, or other proposed diagnosis.

The different kinds of features used in the MVA may, for example, include the illustrative examples of mass spectra and IVD data from patient body fluids, as well as medical imaging data from the patient of interest. Data averaged over a large set of patients other than the patient of interest that have the same medical condition may be generated from the database 30 and used for comparison with data obtained for the patient of interest to arrive at a diagnosis or to monitor disease progression or treatment impact. Features from mass spectra may, for example, be defined as peaks having an intensity above a certain threshold value and a mass within a specified mass interval. From such mass spectral features, true masses or true molecular structures and their corresponding total intensities are optionally computed, assigned to proteins/peptides, and the peak height used to estimate the protein/peptide concentration in the patient sample. In this case, the actual protein/peptide concentration can be used as a feature for the MVA.

The database 30 can be used to construct a MVA once the number of patients for which data are stored is large enough to provide statistically sound MVA. As additional patients are continuously added to the database 30, the MVA can be re-constructed or, alternatively, adjusted based on new patient data. As a result, the references state defined by the database 30 improves continuously with the growing amount of data and provide date within a high-dimensionality space that defines "normal", "ill", "non uncommon", "not pathological", various stages of a disease or treatment impacts, or other possible diagnoses. The features of each patient that is added to the database 30 is suitably compared to the available reference data in the database, for example as embodied by a constructed MVA, in order to generate a proposed diagnosis. The proposed diagnosis may be disease state, grading of a side-effect of a treatment, improvement from a certain treatment, or so forth.

With continuing reference to FIG. 1, the processor 40 is configured to perform MVA as follows. Patient data 50 for a patient of interest (at a given point in time as reflected by the patient data currently stored in the medical database 30) serves as input. The patient data 50 is translated into a multidimensional space by a patient features vector generator 52 that generates a features vector comprising features indicative of the patient of interest derived front the patient medical data 50 which is stored in the database 30 and includes both patient image medical data and patient non-image medical data. The features vector for a patient of interest can be thought of as the representation of the patient of interest in the multidimensional space in which the MVA operates.

Because the database 30 is continuously updated as the patient of interest undergoes various diagnostic imaging and non-image diagnostic tests, in some cases the patient data 50 may be incomplete such that certain elements of the features vector cannot be determined from the available patient data 50. To accommodate missing data, a features padding component 54 pads any feature of the features vector which cannot be derived from the patient medical data 50 with a default value. The output of the components 52, 54 is a features vector 56 comprising features indicative of the patient of interest.

Optionally, the features vector 56 generated for each patient is accumulated in a features vectors database 60. In this way, recomputation of the features vectors can be avoided. If the patient of interest undergoes an additional test, then the features vector 56 can be retrieved from the features vectors database 60, any vector elements affected by the results of the additional test are updated by the components 52, 54, and the updated features vector stored back into the features vectors database 60.

The features vectors stored in the features vectors database 60 are suitably used to construct a multivariate analysis (MVA) to generate a proposed diagnosis. In some embodiments, the MVA is embodied by a classifier that receives and classifies a features vector—in such embodiments, the MVA construction component is suitably embodied as a MVA trainer 62 that trains the classifier using a training set of features vectors for already-diagnosed patients, some of whom have the relevant diagnosis (positive examples) and some of whom do not have the relevant diagnosis (negative examples). The resulting trained classifier then embodies a MVA expert 64.

If the features vector 56 represents a patient of interest for which a proposed diagnosis is desired, then at a branch point 66 the features vector 56 is input to the MVA expert 64 which outputs a proposed diagnosis for the patient of interest. The proposed diagnosis can be displayed on the user interface display 44 or otherwise presented in a human-perceptible output format. The patient of interest is typically not a member of the training set that was used to train the MVA expert 64, since the patient of interest does not have an a priori-known diagnosis and hence is not either a positive training example or a negative training example. However, in some embodiments the proposed diagnosis is accepted or rejected by a physician or other human medical personnel via the user interface 42, and thereafter the features vector 56 for the patient of interest which (now) includes a confirmed diagnosis may be used by the MVA trainer 62 as further training data for refinement of the MVA expert 64.

In sum, the system of FIG. 1 extracts features from images and non-image medical data such as IVD data or mass spectral data, and creates datasets with definition of normal and disease slate multidimensional volumes. A feature set of a new patient is created and compared to site IVD and imaging features of tire database. We suggest to combine the IVD features with the orthogonal image features for each patient. In one embodiment, the results are co-displayed on a screen to assist diagnosis of the doctor. In another embodiment, the features are jointly analyzed resulting in a response value or vector which is the diagnosis.

Figure 2:
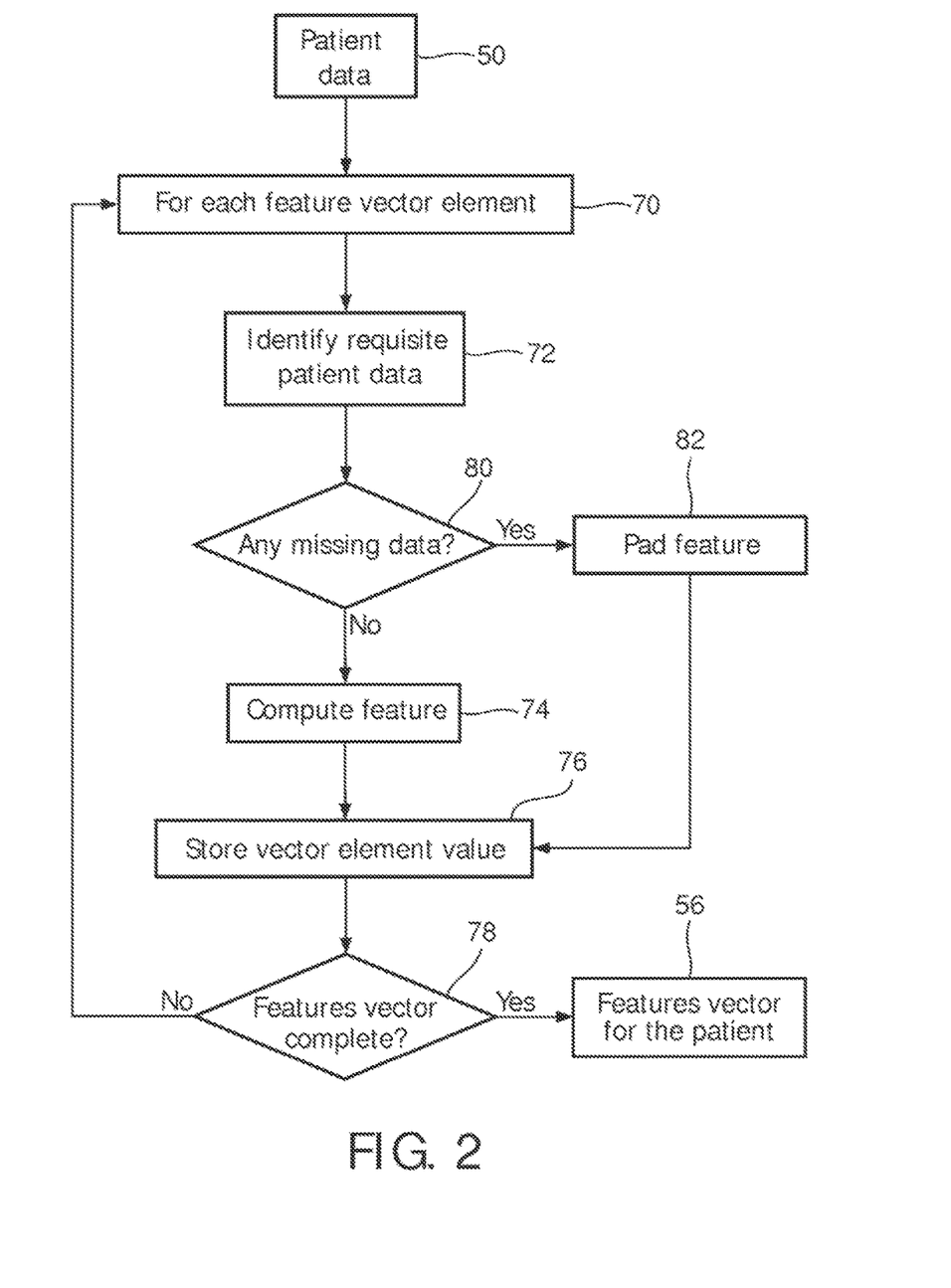
FIG. 2 diagrammatically illustrates a method performed by the apparatus of FIG. 1 to generate a features vector combining image and non-image data for a patient.

With reference to FIG. 2, operation of an illustrative embodiment of the features vector generating component 52 is described. If the multidimensional space in which the MVA operates has N dimensions, then the features vector includes N elements corresponding to the N dimensions. A looping operator 70 selects each vector element in turn for processing. The patient data used in computing the selected vector element is identified in an operation 72, the feature is computed from the identified patient data in an operation 74 and is stored as the vector element value in an operation 76. This processing is repeated 78 for each vector element (or, equivalently, for each dimension of the multidimensional space) to construct the features vector 56.

Figure 3:
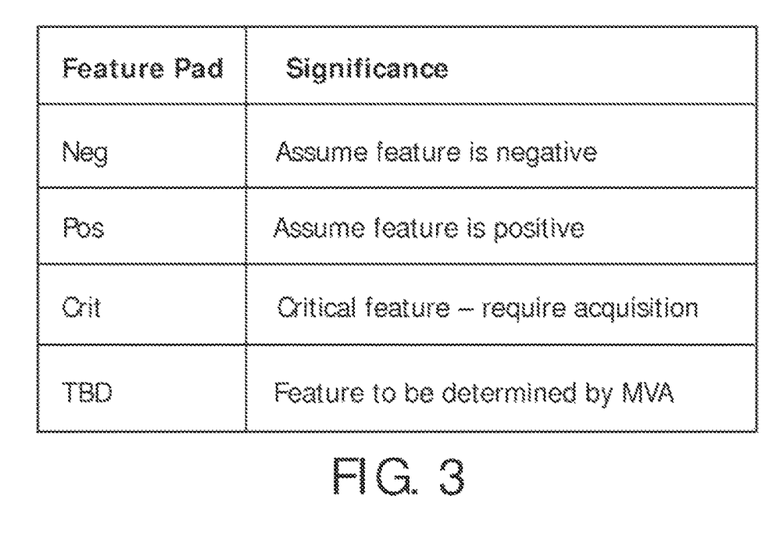
FIG. 3 tabulates some feature pads suitably used to pad features of the features vector for which database data are unavailable or incomplete.

With continuing reference to FIG. 2 and with further reference to FIG. 3, operation of an illustrative embodiment of the features padding component 54 is described. After the relevant patient data identification operation 72 a check 74 is made as to whether any relevant patient data are missing. If no relevant patient data are missing, then the features vector generating component 52 performs the operations 74, 76 as already described. If, however, any relevant patient data are missing, then a padding operation 82 is instead applied to assign a default value for the feature, which is then stored as the vector element value in the operation 76. The default vector element value is suitably chosen based on the type of feature and the particular MVA to be performed. FIG. 3 tabulates some contemplated default values in the case in which the feature is a diagnostic test result. The missing data in this case is the diagnostic test data, without which the diagnostic test result cannot be determined. A "Neg" default value is suitably used to pad the feature if it is advantageous to assume that the unavailable test result is negative. This may be appropriate, for example, if the diagnostic test has a high false positive rate such that a positive result might end up being "ignored" by the MVA anyway. A "Pos" default value is suitably used to pad the feature if it is advantageous to assume that the unavailable test result is positive. This may be appropriate, for example, if the diagnostic test has a high false negative rate such that a negative result might end up being "ignored" by the MVA.

A "Crit" default value is suitably used to pad the feature if the unavailable test result is critical to the diagnosis, such that a proposed diagnosis should not be presented at all in the absence of this critical diagnostic test. For example, in the case of a MVA constructed to estimate the likelihood that a tumor is malignant, a biopsy test on the tumor may be considered to be sufficiently critical that a proposed diagnosis of "malignant" or "benign" should not be presented if the biopsy test result is unavailable.

A "TBD" default value is optionally provided in order to incorporate the proposed diagnosis into the features vector. In some embodiments, the proposed diagnosis is associated with the features vector but is not incorporated into the features vector. In the illustrated embodiment, however, the proposed diagnosis is treated as a vector element of the features vector. An advantage of this approach is that in the case in which a physician or other competent human medical personnel makes the diagnosis without resort to the MVA, this human diagnosis can be incorporated directly into the features vector. In such embodiments, the MVA is only applied to a features vector if a diagnosis is unavailable, which is indicated by the pad value "TBD" for the vector element corresponding to the proposed diagnosis.

Figure 4:
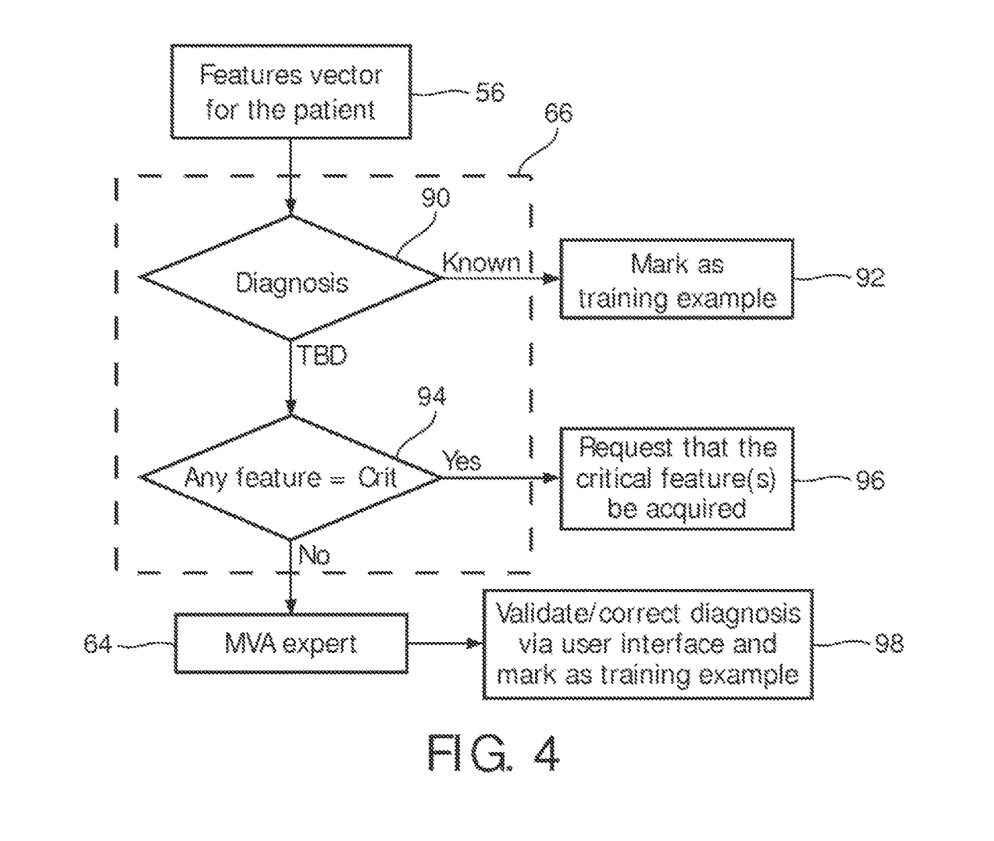
FIG. 4 diagrammatically illustrates a method performed by the apparatus of FIG. 1 to perform multivariate analysis (MVA) of a medical data represented by a features vector for a patient of interest.

With reference to FIG. 4, operation of an illustrative embodiment of the decision point 66 is described. At a first decision block 90 the vector element of the features vector 56 corresponding to the diagnosis is examined. If this vector element already contains a diagnosis value, then the diagnosis is assumed to be "known" and the features vector 56 is optionally marked as a training example in an operation 92. In other Words, in this case there is no need to apply the MVA expert 64 to propose a diagnosis, but the features vector 56 with the a priori-known diagnosis may optionally be used for further training of the MVA expert 64.

On the other hand, if at the first decision block 90 the vector element of the features vector 56 corresponding to the diagnosis is found to contain the default pad "TBD", then it is recognized that no diagnosis is currently available. Accordingly, at a second decision block 94 the remaining vector elements of the features vector 56 are examined to determine if any of these vector elements contain a "Crit" default pad value. If any vector element does contain a "Crit" default pad value, then a request that the critical feature be acquired is made via the user interface 42 in a communication operation 96. For example, in the previous illustration of a MVA constructed to estimate the likelihood that a tumor is malignant, if the texture corresponding to the biopsy test result contains the default pad "Crit" then the operation 96 suggests that a biopsy test should be run, and no proposed diagnosis is provided in the absence of this critical biopsy test.

With continuing reference to FIG. 4, if both decision blocks 90, 94 are passed then it is recognized that a diagnosis is desired and sufficient patient data is available, and accordingly the features vector 56 is input to the MVA expert 64 to generate a proposed diagnosis. In the embodiment of FIG. 4, the proposed diagnosis is presented to the user via the user interface 42 in an output operation 98, and the user can validate (that is, accept) the proposed diagnosis or can correct (or, more generally, reject) the proposed diagnosis. Optionally, the operation 98 also loads the validated diagnosis into the vector element corresponding to site diagnosis (that is, replaces the default pad value "TBD" with the validated diagnosis) and marks the features vector 56 as a training example for optional use in further training of the MVA expert 64.

The MVA expert 64 can be variously embodied depending upon the type of diagnosis to be made and other considerations. In some embodiments the diagnosis is a binary decision—for example, a diagnosis identifying a tumor as either "malignant" or "benign" is a binary decision. For a binary diagnosis, the MVA expert 64 can be embodied as a binary classifier. In other embodiments, the diagnosis has multiple possible values. For example, a diagnosis for a patient suffering from abdominal pain may include numerous possible diagnoses such as "appendicitis", "food poisoning", "abdominal gas", "hernia", and so forth. One approach for constructing the MVA expert 64 to perform a diagnosis having more than two possible diagnoses is to employ a multi-class classifier in which each possible diagnosis corresponds to one possible output of the multi-class classifier. Another approach is to construct the MVA expert 64 to perform a diagnosis having more than two possible diagnoses is to employ a plurality of binary classifiers with each binary classifier corresponding to a specific possible diagnosis and providing a probability of that diagnosis. If the diagnoses are mutually exclusive and span all possible diagnoses, then the probabilities output by the binary classifiers can be normalized to generate an output equivalent to that of a multi-class classifier.

Moreover, the MVA expert 64 can be embodied by algorithms other than classifiers. For example, in another contemplated embodiment the features vectors database 60 is accessed to determine an average or typical features vector for a given diagnosis. For example, this can be done by averaging the values of each vector component over all feature vectors having the given diagnosis. The MVA expert 64 can then compute a distance measure (for example, using a Euclidean distance measure) indicative of the distance between the features vector 56 for the patient of interest and the average or typical features vector for the given diagnosis, so as to provide a quantitative measure of how close the features of the patient of interest are to corresponding features of an "average" patient having the given diagnosis. Optionally, this analysis can further include an element-by-element comparison of the features of the patient of interest and the corresponding features of the "average" patient with the given diagnosis. More generally, data in the form of the features of the features vectors of the database 60 can be averaged over a large set of patients that suffer from a common medical condition and used for comparison with data obtained for a patient of interest (again, in the form of the features vector for the patient of interest) to arrive at a diagnosis or to monitor disease progression or treatment impact.

Another useful analysis optionally performed by the MVA expert 64 is to locate the closest patient (or few closest patients) in the database 30 by searching the features vectors database 60 for the features vector (or few features vectors) that are closest to the features vector 56 in the multidimensional space, as measured by a Euclidean distance measure or other chosen distance measure formulation.

It is to be appreciated that although the single MVA expert 64 is illustrated in diagrammatic FIG. 1, there can in practice be numerous MVA experts each trained or otherwise constructed to perform a selected multivariate analysis directed toward a particular diagnosis. The various MVA experts can utilize the same features vectors or can utilize different features vectors. In some embodiments, the same features vectors are used by all the MVA experts, but suitable features selection processing is performed to select a subset of the features for use by each MVA expert. Suitable features selection processing may include filtering to identify discriminative features, filtering to remove redundant features, or so forth. For example, principle component analysis (PCA) is a known approach for features selection.

Various identification schemes can be used to identify the patients in the databases 30, 60. In one approach, each patient is assigned a unique patient identification number. This advantageously facilitates patient anonymity when, for example, a "closest patient" is identified based on distance from the features vector 56. Optionally, patient name or other identifying patient information is also included in the databases 30, 60. In this latter case, the user interface 42 preferably includes suitable security procedures, such as a login procedure and optional biometric identification (e.g., a fingerprint reader) to ensure that only authorized persons are allowed access to patient-identifying information.

In the following, a more detailed illustrative example is set forth using radiation therapy for treating prostate cancer as the illustrative medical condition. Here, image features may include: the distance between critical organs such as the rectum, bladder or prostate; organ-specific dimensions such as intestinal wall thickness, prostate diameter, prostate volume; or so forth. Relevant non-image features may be extracted from mass spectrometry measurements 20 or IVD tests 22. Image-based features that are expected to correlate with tumor response to the radiation therapy include, for example: lesion volume; lesion metabolism and proliferation as assessed by FDG-PET or other functional imaging; cellular integrity as assessed for instance by diffusion-weighted MR; or so forth. Many of these features are also expected to correlate with inflammation and radiation toxicity of healthy tissue in the critical organs. Predictive image-derived features of tumor response include: sizes/volumes; dose-volume histograms (DVHs); morphological features like textures; surface structure regularity or irregularity; and so forth. Molecular features of interest for prostate cancer therapy include extend of hypoxia as assessed for example by FMISO-PET. To determine such features, image processing algorithms can be applied, such as volume delineation techniques and frequency analysis. Dynamic imaging of contrast agents provides slopes and, in case of pharmacokinetic modelling, rate constants of tracer biodistributions.

Through continuous temporary data storage, a multi-dimensional space of data is achieved. First and second dimensions of the multidimensional space (or, equivalently, first and second elements of the features vector) may, for example, represent a volume and a dose derived from a planning CT. Third and fourth dimensions may represent the concentrations of an IVD marker in patient serum and urine samples and fifth to tenth dimensions may represent a mass spectrometric protein pattern or one or more of its features (peak intensity at certain peak positions). The multidimensional space is analyzed using mathematical algorithms resulting in real molecule masses in the patient samples and/or individual treatment risks.

The data stored in the diagnostic medical database 30 and represented on a per-patient basis by the features vectors of the database 60 are jointly analyzed by the MVA expert 64. Toward this end, features are automatically extracted from the data originating from one patient by the components 52, 54 to generate the features vector 56 for the patient. The extracted features vectors are stored in the database 60. Typical imaging features for prostate cancer applications may be quantitative or qualitative and include DVHs from radiotherapy planning CTs, planning volume, prostate volume, bladder volume, rectum volume, total dose, fraction dosis, SUVs, etc. Mass spectral features are peaks having an intensity over a certain threshold value and a mass within a specified mass interval. From these mass spectral features, true masses or true molecular structures and their corresponding total intensities can be computed and assigned to proteins/peptides and their concentrations in the patient sample. Typical IVD features include concentration of molecules in biologically relevant fluids, e.g. of C-reactive protein (CRP), blood cell counts, and haemoglobin concentration (Hb) after correction using the corresponding reference values. However, a feature may also be a composite, originating from imaging as well as molecular diagnostic data. Features (imaging as well as molecular) which are similar in all patients can be used as internal references. Mathematical combination of features that are similar in many patients can be used to define a standard for comparison. On the other hand, features that are similar in many patients may advantageously be removed by suitable features selection processing prior to constructing the MVA expert 64.

The features from a patient of interest are analyzed for correlations between features. Furthermore, from a common or joint evaluation of features of different origins, a patient-specific treatment complication risk can be computed and a risk stratification can be made. When data from a new patient or a new time point is stored in the database and subsequently analyzed, a best fit to already stored data is automatically identified, and a side-effect risk, treatment recommendation, or other diagnosis is computed.

It will also be appreciated that the diagnostic techniques disclosed herein can be embodied as a storage medium storing instructions executable on the digital processor 40 to perform the disclosed diagnostic techniques. Such a storage medium may include, for example: a hard disk or other magnetic storage medium; an optical disk or other optical storage medium; random access memory (RAM), read-only memory (ROM), flash memory, or another electrostatic storage medium; or so forth.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. An apparatus comprising:
a database that is configured to store medical data of a plurality of patients, the medical data of each patient including medical image data and non-image medical data;
a multivariate analysis (MVA) engine that is configured to:
receive a features vector that is a representation of the patient in a multidimensional space in which the MVA engine operates, and
provide at least one diagnosis based on the values of the features vector;
a vector generator that is configured to:
receive the medical data of a patient of interest from the database,
provide a feature value corresponding to each feature of the features vector from the patient's medical data, and
provide the features vector to the MVA engine to obtain the at least one diagnosis; and
a user interface that is configured to provide the at least one diagnosis to a user;
wherein:
the vector generator is configured to identify a feature for which the medical data of the patient is insufficient to obtain a missing feature value;
the apparatus includes a padding component that is configured to provide a default value as the missing feature value, the default value being a value that is not expected to have an effect on the diagnosis provided by the MVA engine; and
the padding component is configured to alert the user that a default value cannot be provided when any default value for the missing feature value is expected to change the diagnosis provided by the MVA engine.

2. The apparatus of claim 1, wherein the missing feature value is an outcome of a given binary test having a "positive" or "negative" outcome, and the padding component is configured to provide the default value based on a proportion of "false negatives" and "false positives" associated with the given binary test.

3. The apparatus as set forth in claim 1, wherein the MVA engine includes one or more binary classifiers, and wherein each binary classifier outputs a probability of a corresponding diagnosis.

4. The apparatus of claim 1, wherein the at least one diagnosis includes one or more diagnoses selected from a group consisting of a medical condition, a stage of a medical condition, a treatment side effect, and a treatment response.

5. The apparatus of claim 1, wherein the MVA engine is based on features vectors of a plurality of patients other than the patient of interest having one or more confirmed diagnoses.

6. The apparatus of claim 5, wherein the MVA engine includes at least one classifier and is configured by training the at least one classifier using a training set of the features vectors of the plurality of patients other than the patient of interest, wherein the features vectors of the training set include or are associated with diagnoses, treatment side-effects, or treatment responses.

7. The apparatus as set forth in claim 1, wherein the feature generator is configured to request additional patient data from the user to determine the missing feature value.

8. A diagnostic method comprising:
maintaining a database storing medical data including image medical data and non-image medical data for a plurality of patients;
generating, by a digital processor, features vectors corresponding to patients of the database, each features vector includes values of features indicative of the corresponding patient derived from medical data for the corresponding patient stored in the database;
accessing a multivariate analysis (MVA) engine that is configured to receive a features vector of a patient of interest, and provide at least one diagnosis based on the values of the features vector;
enabling a padding component that assesses the features of the features vector of the patient of interest to determine if any feature has a missing feature value for use in the MVA engine based on the patient's medical data, and provides a default value as the missing feature value;
providing the features vector to the MVA engine to obtain the at least one diagnosis based on the features vector of the patient of interest; and
providing the at least one diagnosis to a user;
wherein:
the padding component:
provides a default value as the missing feature value, the default value being a value that is not expected to have an effect on the diagnosis provided by the MVA engine; and
alerts the user that a default value cannot be provided when any default value for the missing feature value is expected to change the diagnosis provided by the MVA engine.

9. The diagnostic method of claim 8, wherein the missing feature value is an outcome of a given binary test having a "positive" or "negative" outcome, and the padding component is configured to provide the default value based on at least one of a "false negatives" rate and a "false positives" rate associated with the given binary test.

10. The diagnostic method of claim 8, including constructing the MVA engine, wherein the constructing comprises: training one or more classifiers embodying the MVA engine using a training set of features vectors for patients of the database other than the patient of interest having one or more confirmed diagnoses.

11. The diagnostic method of claim 8, further including: simultaneously displaying a human-perceptible representation of one or more features of the features vector corresponding to the patient of interest.

12. The diagnostic method of claim 8, wherein the image medical data are acquired from a picture archiving and communication service (PACS).

13. A non-transitory computer readable medium that includes a program that, when executed by a processing system, causes the processing system to:
access a database storing medical data including image medical data and non-image medical data for a patient of interest;
generate a features vector corresponding to patient of interest, the values of features in the features vector being indicative of the corresponding patient, being derived from medical data for the patient of interest stored in the database;
assess a multivariate analysis (MVA) engine to identify features of a features vector that is a representation of a patient in a multidimensional space in which the MVA engine operates;
enable a padding component that assesses the features of the features vector of the patient of interest to determine if any feature has a missing feature value for use in the MVA engine based on the patient's medical data, and provides a default value as the missing feature value;
enable the multivariate analysis (MVA) engine to receive the features vector of the patient of interest, and provide at least one diagnosis based on the values of the features vector;
provide the at least one diagnosis to a user;
wherein:
via the padding component, the program causes the processing system to:
provide the default value as a value that is not expected to have an effect on the diagnosis provided by the MVA engine; and
alert the user that the default value cannot be provided when any default value for the missing feature value is expected to change the diagnosis provided by the MVA engine.

14. The medium of claim 13, wherein the missing feature value is an outcome of a given binary test having a "positive" or "negative" outcome, and the program causes the processing system to provide the default value based on at least one of a "false negatives" rate and a "false positives" rate associated with the given binary test.

15. The medium of claim 13, wherein the computer causes the processing system to construct the MVA engine, wherein constructing the MVA engine includes: training one or more classifiers embodying the MVA engine using a training set of features vectors for patients of the database other than the patient of interest having one or more confirmed diagnoses.

16. The medium of claim 13, wherein the computer causes the processing system to simultaneously display a human-perceptible representation of one or more features of the features vector corresponding to the patient of interest.

17. The medium of claim 13, wherein the image medical data are acquired from a picture archiving and communication service (PACS).

* * * * *